(12) United States Patent
Tanimoto et al.

(10) Patent No.: US 8,673,245 B2
(45) Date of Patent: Mar. 18, 2014

(54) FIXED-BED REACTOR AND PROCESS FOR PRODUCING ACRYLIC ACID USING THE REACTOR

(75) Inventors: Michio Tanimoto, Himeji (JP); Nobuyuki Hakozaki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 361 days.

(21) Appl. No.: 13/056,416

(22) PCT Filed: Sep. 9, 2009

(86) PCT No.: PCT/JP2009/065750
§ 371 (c)(1),
(2), (4) Date: Jan. 28, 2011

(87) PCT Pub. No.: WO2010/032665
PCT Pub. Date: Mar. 25, 2010

(65) Prior Publication Data
US 2011/0178334 A1    Jul. 21, 2011

(30) Foreign Application Priority Data
Sep. 22, 2008 (JP) .................................. 2008-242064

(51) Int. Cl.
*B01J 8/04* (2006.01)
*B01J 8/06* (2006.01)
*C07C 51/16* (2006.01)

(52) U.S. Cl.
USPC ............ 422/635; 422/630; 422/631; 422/638; 422/644; 422/652; 422/653; 562/531

(58) Field of Classification Search
USPC ......... 422/630, 635, 638, 644, 652, 653, 631; 261/94; 562/531
See application file for complete search history.

(56) References Cited

U.S. PATENT DOCUMENTS 3,430,934 A * 3/1969 Weishaupt ................. 261/94
(Continued)

FOREIGN PATENT DOCUMENTS

| JP | 54-21966 | 2/1979 |
| JP | 1-165543 | 6/1989 |

(Continued)

OTHER PUBLICATIONS

International Search Report issued Oct. 13, 2009 in corresponding International Application No. PCT/JP2009/065750, of record.

*Primary Examiner* — Lessanework Seifu
(74) *Attorney, Agent, or Firm* — Wenderoth, Lind & Ponack, L.L.P.

(57) ABSTRACT

A fixed-bed reactor containing a first catalyst layer filled with a first catalyst for producing acrolein from propylene; a second catalyst layer filled with a second catalyst for producing acrylic acid from acrolein; and an inert substance layer provided between the first catalyst layer and the second catalyst layer, and filled with an inert substance of a cylindrical shape having a surrounding wall in which an opening is formed. A process for producing acrylic acid containing the step of producing acrylic acid from propylene by using the aforementioned fixed-bed reactor.

12 Claims, 1 Drawing Sheet

(56) References Cited

U.S. PATENT DOCUMENTS

| | | |
|---|---|---|
| 4,203,906 A | 5/1980 | Takada et al. |
| 4,256,783 A | 3/1981 | Takada et al. |
| 4,579,599 A * | 4/1986 | Takeda .................. 134/25.1 |
| 6,069,271 A | 5/2000 | Tanimoto et al. |
| 6,624,114 B1 * | 9/2003 | Eberle et al. .................. 502/439 |
| 7,238,836 B2 * | 7/2007 | Ha et al. .................. 562/545 |
| 7,884,235 B2 | 2/2011 | Tanimoto et al. |
| 2008/0021240 A1 | 1/2008 | Tanimoto et al. |

FOREIGN PATENT DOCUMENTS

| | | |
|---|---|---|
| JP | 6-170232 | 6/1994 |
| JP | 11-33393 | 2/1999 |
| JP | 11-130722 | 5/1999 |
| JP | 2008-24644 | 2/2008 |

* cited by examiner (a)

(b)

(c)

(d)

FIXED-BED REACTOR AND PROCESS FOR PRODUCING ACRYLIC ACID USING THE REACTOR

TECHNICAL FIELD

The present invention relates to a fixed-bed reactor suitable for producing acrylic acid from propylene by two-stage gas-phase catalytic oxidation, an inert substance used for the fixed-bed reactor, and a process for producing acrylic acid using the fixed-bed reactor.

BACKGROUND ART

The most common process for producing acrylic acid is a two-stage gas-phase catalytic oxidation process, which is widely used industrially. This process includes a first reaction of producing acrolein from propylene by gas-phase catalytic oxidation and a second reaction of producing acrylic acid from acrolein by gas-phase catalytic oxidation. Conventionally, for conducting such a reaction, there have been proposed roughly two methods: a method using two reactors, that is, a first reactor filled with a catalyst suitable for a first reaction (hereinafter referred to as a "first catalyst") and a second reactor filled with a catalyst suitable for a second reaction (hereinafter referred to as a "second catalyst"); and a method using one reactor which includes a first reaction zone filled with the first catalyst and a second reaction zone filled with the second catalyst.

A process for producing acrylic acid from propylene by two-stage gas-phase catalytic oxidation has problems such as obstruction of a reaction tube induced by sublimates from the first reaction, more specifically, a molybdenum component sublimed from a molybdenum-containing oxide catalyst that is generally used as the first catalyst, or high-boiling substances such as terephthalic acid by-produced in the first reaction, and increase of pressure loss. Various proposals have been made about a process for producing acrylic acid more efficiently by remedying these problems.

For example, Patent Literature 1 discloses a process for producing acrylic acid from propylene by two-stage gas-phase catalytic oxidation, in which the first catalyst and the second catalyst are respectively filled into each of two reactors, that is, a primary reactor and a secondary reactor, and a rod-like or plate-like insertion object is inserted into a gas inlet space of the second catalyst so that the void ratio in the tube is 40% or more and 90% or less.

Patent Literature 2 discloses a process for producing acrylic acid using one fixed-bed multitubular heat-exchanging reactor. In Patent Literature 2, the first catalyst and the second catalyst are respectively filled into a lower part and an upper part of each of reaction tubes of the reactor to form a first catalyst layer and a second catalyst layer, and an inert substance is filled into the space between the first catalyst layer and the second catalyst layer so that the void ratio is 40% or more and 99.5% or less. Here, the inert substance layer is provided so as to have a sufficient length for cooling a reaction gas from the first catalyst layer to a temperature suitable for introducing into the second catalyst layer, and further, both the catalyst situated at an upper end part of the first catalyst layer and the catalyst situated at a lower end part of the second catalyst layer are disposed at positions where they are not substantially affected by heat from a partition plate. Acrylic acid is produced by introducing a raw material gas containing propylene from lower parts of the reaction tubes to pass through as an upward flow.

Patent Literature 3 discloses a method in which, upon conducting a gas-phase catalytic oxidation reaction, a treatment agent for removing organic matters and/or carbides is disposed at an upstream side of a gas-phase oxidation catalyst layer relative to the gas flow, and the treatment agent is exchanged at a frequency of at least once a year.

Patent Literature 4 discloses, in Example 5, that two-stage gas-phase catalytic oxidation is conducted using one multitubular heat-exchanging reactor by introducing a raw material gas containing propylene from a top of each of reaction tubes of the reactor. In Patent Literature 4, into each reaction tube of the reactor, the second catalyst is firstly filled to form a second catalyst layer, then alundum for cooling a reaction gas is filled on the second catalyst layer, and finally the first catalyst is filled on the alundum layer to form a first catalyst layer. And, the two-stage gas-phase catalytic oxidation is conducted by introducing a raw material gas containing propylene from the top of the reaction tube.

Patent Literature 5 discloses a process for producing unsaturated carboxylic acid by introducing unsaturated aldehyde into a catalyst layer filled with an uniform mixture of a catalyst containing molybdenum and vanadium, and Raschig rings made of a metal that have a bulk volume of 0.3 times to 3.5 times that of the catalyst and a filling density of 0.5 kg/l to 1.5 kg/l, to perform gas-phase catalytic oxidation.

CITATION LIST

Patent Literature

Patent Literature 1
  Japanese Unexamined Patent Application Publication No. 1-165543
Patent Literature 2
  Japanese Unexamined Patent Application Publication No. 11-130722
Patent Literature 3
  Japanese Unexamined Patent Application Publication No. 2008-24644
Patent Literature 4
  Japanese Unexamined Patent Application Publication No. 54-21966
Patent Literature 5
  Japanese Unexamined Patent Application Publication No. 11-33393

SUMMARY OF INVENTION

Technical Problem

Acrylic acid is produced as much as several millions of tons per year worldwide presently and enhancing an yield of acrylic acid in an industrial scale by just 0.1% would have a significant meaning in terms of economy. Furthermore, it would be all the more significant if acrylic acid can be produced stably over a longer period. Although all the above-mentioned production processes are improved in terms of about the yield of acrylic acid and the production over a long period, there is still room for improvement in view of recent jumps in raw material prices and higher load of reaction conditions owing to growing demand.

In Patent Literature 1, a certain degree of effect is obtained by inserting the plate-like insertion object made of a metal or ceramic into the inlet of the secondary reactor to prevent obstruction in the catalyst layer in the secondary reactor due to by-products. However, even though it is possible to prevent obstruction itself by the plate-like insertion object made of a metal or ceramic, not a little amount of organic matters or carbides is adhered or deposited onto the catalyst. Thus, when the reaction is conducted for a longer period, the catalyst performance is highly likely to deteriorate due to adherence or deposition of organic matters or carbides. Therefore, the process of Patent Literature 1 has not reached a satisfactory level. Patent Literature 1 also discloses that a Raschig ring made of stainless-steel does not provide such an effect at all whereas a plate-like insertion object is suitable.

In Patent Literature 2, a certain degree of effect is obtained by providing the inert substance layer having the void ratio of 40% or more and 99.5% or less between the first catalyst layer and the second catalyst layer to prevent not only increase of pressure loss but also deterioration in catalyst performance due to direct entering of by-produced high-boiling substances and the like into the second catalyst layer. As to the reaction conditions, however, the space velocity (SV) of propylene relative to the first catalyst is 90 (1/hour) at most and there is unknown about the effect under the recent highly-loaded conditions. In addition, Patent Literature 2 describes that a simple Raschig ring is optimal as the inert substance to be used and discloses only examples in which the Raschig ring made of stainless-steal is used.

Also in Patent Literature 3, a raw material propylene concentration in the examples is 5% at most and the treatment agent filled should be exchanged at least once a year. Therefore, when a reaction is conducted at a high load, the exchange frequency of the treatment agent increases and the reaction is forced to stop for the exchange. Further, in the case that the reaction is performed in one reactor, at least either of the first catalyst or the second catalyst should be discharged when exchanging the treatment agent filled between the first catalyst layer and the second catalyst layer. This is likely to increase the cost in production of acrylic acid.

Patent Literature 4 discloses, in Example 5, that alundum for cooling a reaction gas is filled between the first catalyst layer and the second catalyst layer. However, Patent Literature 4 neither suggests nor examines nor considers the problem of obstruction of the reaction tube due to sublimates from the first catalyst, by-produced high-boiling substances in the first reaction and the like, and increase of the pressure loss.

Patent Literature 5 aims to suppress powdering or disruption of a catalyst due to physical impact upon filling the catalyst by dropping and to prevent generation of hot spots during the reaction by uniformly mixing and filling the catalyst and the Raschig rings made of a metal. In other words, Patent Literature 5 does not relate to an inert substance to be filled between the first catalyst layer and the second catalyst layer, and neither even suggests nor examines the problem of obstruction of the reaction tube due to sublimates from the first catalyst, by-produced high-boiling substances and the like, and increase of the pressure loss.

The present invention has been achieved in view of the above circumstances, and an object of the present invention is to provide a fixed-bed reactor and a process for producing acrylic acid which can produce acrylic acid at a high yield stably for a longer period in producing acrylic acid by two-stage gas-phase catalytic oxidation of propylene even in a highly-loaded condition in an industrial scale.

Solution to Problem

The fixed-bed reactor of the present invention which solves the above problems is a fixed-bed reactor comprising: a first catalyst layer filled with a first catalyst for producing acrolein from propylene; a second catalyst layer filled with a second catalyst for producing acrylic acid from acrolein; and an inert substance layer provided between the first catalyst layer and the second catalyst layer, and filled with an inert substance of a cylindrical shape having a surrounding wall in which an opening is formed. In addition, the process for producing acrylic acid of the present invention is a process for producing acrylic acid comprising the step of producing acrylic acid from propylene by using the fixed-bed reactor of the present invention. According to the present invention, since the inert substance of a cylindrical shape having a surrounding wall in which an opening is formed is used as an inert substance, increase of the pressure loss can be drastically suppressed, degradation of the catalyst due to by-produced high-boiling substances and the like can be suppressed, and further the yield of acrylic acid can be enhanced, as compared with the case of using conventional inert substances. Accordingly, it is possible to produce acrylic acid at a high yield stably for a long period.

Advantageous Effects of Invention

According to the present invention, in producing acrylic acid by two-stage gas-phase catalytic oxidation of propylene, stable production at a higher yield is made possible for a long period as compared with conventional processes.

BRIEF DESCRIPTION OF DRAWINGS

FIG. 1(a) shows a schematic view of an inert substance of which one opening is formed in the surrounding wall. FIG. 1(b) shows a schematic view of an inert substance of which two openings are formed in the surrounding wall. FIG. 1(c) shows a schematic view of an inert substance of which three openings are formed in the surrounding wall. FIG. 1(d) shows a schematic view of an inert substance of which four openings are formed in the surrounding wall.

DESCRIPTION OF EMBODIMENTS

Figure 1:
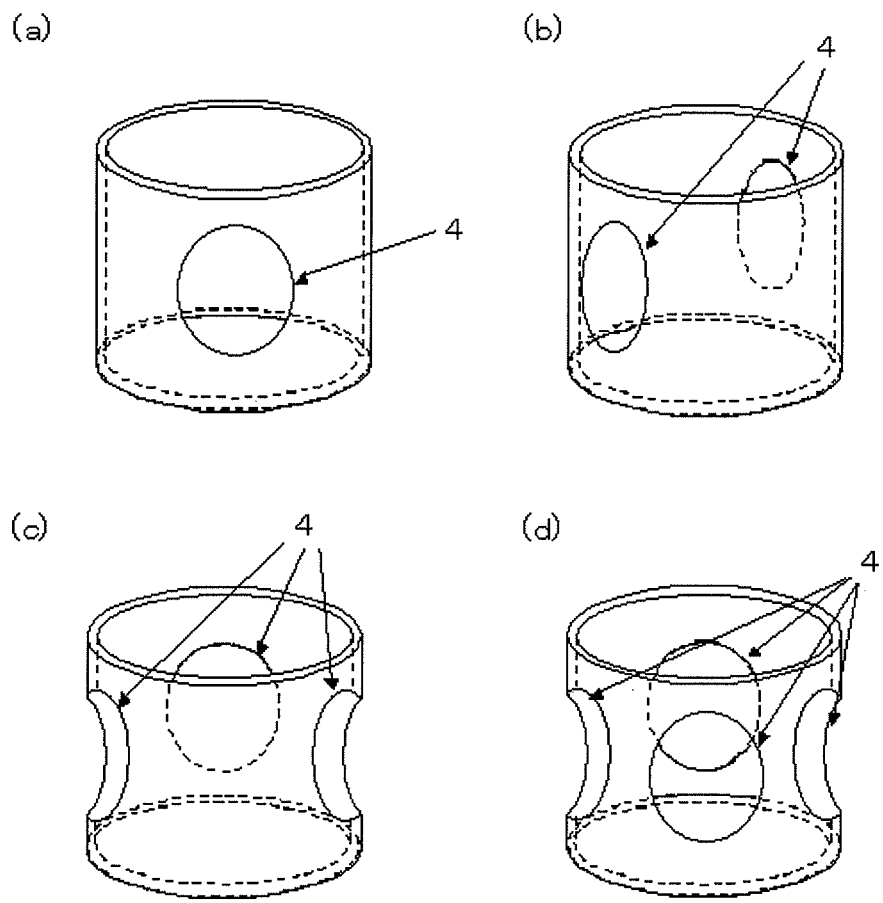
FIG. 1 shows schematic views of inert substances used in the present invention, of each of which an opening is formed in the surrounding wall.

The present invention will hereinafter be explained in detail; however, the present invention is not limited to the following description, and can be put into practice after appropriate modification or variations within a range meeting the gist of the present invention in addition to the following embodiments.

A fixed-bed reactor of the present invention comprises a first catalyst layer filled with a first catalyst for producing acrolein from propylene, a second catalyst layer filled with a second catalyst for producing acrylic acid from acrolein, and an inert substance layer provided between the first catalyst layer and the second catalyst layer and filled with an inert substance. A well-known fixed-bed reactor can be used for the fixed-bed reactor of the present invention, except that the inert substance has a cylindrical shape having a surrounding wall in which an opening is formed. Thus, the present invention is characterized in that the inert substance of a cylindrical shape having a surrounding wall in which an opening is formed, is used for being filled into the inert substance layer of a fixed-bed reactor for producing acrylic acid by two-stage gas-phase catalytic oxidation of propylene.

The fixed-bed reactor may be composed of one reactor provided with a reaction tube having a first reaction zone filled with the first catalyst and a second reaction zone filled with the second catalyst. In this case, the first reaction zone corresponds to the first catalyst layer and the second reaction zone corresponds to the second catalyst layer, and the inert substance layer is provided between the first reaction zone and the second reaction zone. Thus, at least three layers composed of the first catalyst layer, the inert substance layer and the second catalyst layer are provided in one reaction tube.

The fixed-bed reactor may be composed of two reactors, that is, a first reactor provided with a reaction tube filled with the first catalyst and a second reactor provided with a reaction tube filled with the second catalyst. In this case, a part of the reaction tube in the first reactor, into which the first catalyst is filled, corresponds to the first catalyst layer, and a part of the reaction tube in the second reactor, into which the second catalyst is filled, corresponds to the second catalyst layer. The inert substance layer may be disposed closer to an outlet side of the first reactor than the first catalyst layer, or may be disposed closer to an inlet side of the second reactor than the second catalyst layer, or may be disposed in a pipe connecting the first reactor and the second reactor. Here, the "inlet side" and the "outlet side" mean a side of the reactor into which gas is introduced and a side of the reactor from which gas is discharged, respectively.

The inert substance used in the present invention is explained. The inert substance used in the present invention is not particularly limited as long as it is substantially inert to a reaction gas containing acrolein and has a cylindrical shape having a surrounding wall in which an opening is formed. The reaction gas may possibly contain propylene as a raw material, by-products such as terephthalic acid and the like, and impurities.

The cylindrical shape means a so-called straight pipe shape or a ring shape. The surrounding wall is formed so as to surround an axial direction of the cylindrical shape and end faces are formed so as to cross the axial direction. Since the surrounding wall has some thickness, it has an outer surface and an inner surface, and thus, the end face also has an outer circumference and an inner circumference.

The angle at which the end face of the cylindrical shape crosses the axial direction is not particularly limited. The end face may be flat or may be meandered or zigzag-shaped, for example. However, in view of increasing the void ratio of the inert substance layer and facilitating the production and processing of the inert substance, the end face of the cylindrical shape is preferably flat and orthogonal to the axial direction.

Examples of a cross-sectional shape of the cylindrical shape include a circular shape, an elliptical shape, a closed irregular curved shape, and the like. Therefore, the inert substance does not have any structures inside the inner surface and outside the outer surface of the surrounding wall of the cylindrical shape. The cross-section of the cylindrical shape means a part obtained by cutting the cylindrical shape along a plane orthogonal to the axial direction.

Preferably, the cross-sectional shape of the cylindrical shape is a substantially circle. Here, the substantially circular shape means a shape in which, when the outer circumference is placed in between two concentric circles (a circumscribed circle and an inscribed circle), the difference (f) in radius between the circumscribed circle and the inscribed circle at a position where the distance between the circumscribed circle and the inscribed circle is the smallest is 0.2 or less relative to the radius (R) of the circumscribed circle. The f/R ratio is 0.2 or less also for the inner circumference. The f/R ratio of the outer circumference and the inner circumference is preferably 0.1 or less. It is more preferred that the f/R ratio is closer to 0 since the cross-sectional shape comes closer to a circle.

When the cross-sectional shape of the cylindrical shape is substantially circular, it becomes easy to increase the void ratio of the inert substance layer while maintaining the mechanical strength of the inert substance and reduce the pressure loss of the inert substance layer.

The cylindrical shape is more preferably a hollow cylindrical shape. That is, it is preferred that the cylindrical shape is formed such that the end face is flat and orthogonal to the axial direction and the cross-section has a substantially circular shape. Such a cylindrical shape easily enables increasing the void ratio of the inert substance layer while maintaining the mechanical strength of the inert substance and facilitating the production of the inert substance.

Figure 2:
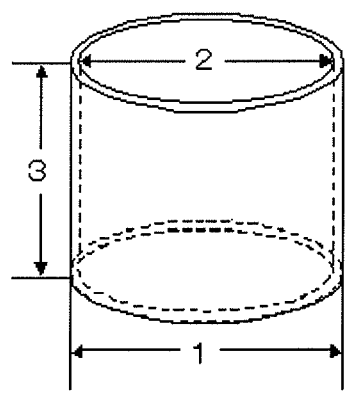
FIG. 2 shows a schematic view of a conventionally-used inert substance.

The cylindrical shape preferably has an outer diameter of 3.0 mm or more and 10.0 mm or less, a length in the axial direction of 0.5 times or more and 2.0 times or less as much as the outer diameter, and an inner diameter of 0.5 times or more and 0.95 times or less as much as the outer diameter. Here, in the present invention, the outer diameter is defined as an average value of diameters of the circumscribed circle and the inscribed circle of the outer circumference, and the inner diameter is defined as an average value of diameters of the circumscribed circle and the inscribed circle of the inner circumference. When the cylindrical shape has the above-mentioned size, the inert substance can be suitably filled into reaction tubes of a general fixed-bed reactor. More preferably, the cylindrical shape is a Raschig ring shape in which the length in the axial direction and the outer diameter are the same, which are each 3.0 mm or more and 10.0 mm or less, and the inner diameter is 0.7 times or more and 0.95 times or less as much as the outer diameter. Here, an inert substance having a cylindrical shape without an opening as a conventionally-used inert substance is shown in FIG. 2, in which the lengths of the outer diameter and the inner diameter and length in the axial direction are respectively denoted by reference numerals 1, 2 and 3.

An opening is formed in the surrounding wall of the cylindrical shape. When the inert substance of the cylindrical shape having the surrounding wall in which an opening is formed, increase of the pressure loss in the inert substance layer in a fixed-bed rector is suppressed in producing acrylic acid from acrolein by two-stage gas-phase catalytic oxidation. In addition, degradation of the second catalyst caused by introduction of impurities contained in the reaction gas, such as molybdenum component sublimed from the first catalyst and by-produced high-boiling substances, into the second catalyst layer is suppressed.

A shape of the opening is not particularly limited, and may be a circular shape, an elliptical shape, a triangular shape, a quadrangular shape, an irregular shape, or the like. Furthermore, the opening is not limited to a hole and may be a notch. For example, the inert substance may have a coil shape, namely, the cylindrical shape with a spiral notch formed on the whole surrounding wall thereof. However, in view of increasing the void ratio of the inert substance layer, the opening is preferably a hole. In addition, in view of ease of forming the opening, the shape of the opening is preferably circular.

The opening is not formed by, for example, linearly cutting a part of the surrounding wall and tucking the cut part inside the surrounding wall. When the cut part of the surrounding wall is tucked inside or outside the surrounding wall, it is not preferred since sublimates from the first catalyst, by-produced high-boiling components and the like tend to deposit onto the tucked part. That is, there is no structure inside the inner surface and outside the outer surface of the surrounding wall of the cylindrical shape and the opening is formed by removing a part of the surrounding wall.

A number of the opening formed in the surrounding wall is not limited; however, it is preferably about 2 or more and 6 or less. FIG. 1 shows examples of the inert substance used in the present invention. In FIG. 1, the surrounding wall of the cylindrical shape is provided with from one to four openings (indicated by reference numeral 4) of a circular shape.

The surrounding wall of the cylindrical shape preferably has an opening ratio of 0.04 or more and 0.60 or less. In the present invention, the opening ratio is defined as follows. In the following definitional formula, each area refers to an area in the state of a flat surface obtained by cutting the surrounding wall of the cylindrical shape in the axial direction and developing the cut wall. When there are a plurality of openings, the "area of the opening" means the sum of the areas of all the openings. The "areas of the outer surface of the surrounding wall and the opening" means the sum of the area of the opening and the area of the outer surface of the surrounding wall, and is the area of the outer surface of the surrounding wall of the cylinder assuming that no opening is formed.

Opening ratio=an area of the opening/areas of an outer surface of the surrounding wall and the opening When the opening ratio is less than 0.04, increase of the pressure loss in the inert substance layer may be insufficiently suppressed and degradation of the catalyst caused by deposition of molybdenum component sublimed from the first catalyst, by-produced high-boiling substances and the like in the second catalyst layer may be is insufficiently suppressed. On the other hand, when the opening ratio is more than 0.60, the mechanical strength of the inert substance itself may come to deteriorate and the inert substance easily loses shape in filling, resulting in causing increase of the pressure loss. Further, it is disadvantageous also in view of economical effect when the inert substance loses shape in discharging from the reactor, thereby becoming unable to be recycled. The opening ratio is more preferably 0.06 or more and 0.40 or less.

That is, it is only necessary for the inert substance used in the present invention to be, possibly filled or placed into the reaction tube, have a cylindrical shape, and have one or more opening in the surrounding wall of the cylindrical shape. More preferably, the inert substance has a cylindrical shape in which the outer diameter is 3.0 mm or more and 10.0 mm or less, the length in the axial direction is 0.5 times or more and 2.0 times or less as much as the outer diameter, and the inner diameter is 0.5 times or more and 0.95 times or less as much as the outer diameter, and the opening ratio thereof is 0.04 or more and 0.60 or less. Further preferably, the inert substance has a Raschig ring shape in which the length in the axial direction and the outer diameter are the same, which are each 3.0 mm or more and 10.0 mm or less, and the inner diameter is 0.7 times or more and 0.95 times or less as much as the outer diameter, and the opening ratio thereof is 0.06 or more and 0.40 or less.

A material of the inert substance is not particularly restricted as long as it does not substantially affect the reaction. Examples of the material of the inert substance include, for example, α-alumina, alundum, mullite, carborundum, silicon carbide, steatite, earthenware, porcelain, stainless-steel (SUS), iron, various ceramics, and the like. From the viewpoint of heat conductivity and corrosion resistance, it is particularly preferred that the inert substance is made of stainless-steel. The kind of the stainless-steel is not particularly limited. For example, stainless-steel of SUS 400 series is preferably used as the inert substance, since it can be easily separated and recovered from a catalyst by a magnet due to its magnetic property and thus can be easily recycled after use. Examples of SUS 400 series include SUS403, SUS405, SUS410, SUS430, SUS434 and the like.

The inert substance used may be either new or a recycled inert substance. When impurities or the like are attached to the surface of the inert substance, it is preferred to wash and/or heat the inert substance to remove the impurities or the like.

The inert substance is filled into the inert substance layer. The inert substance does not necessarily have to be filled uniformly into the whole inert substance layer; however, in view of preventing autoxidation of an acrolein-containing reaction gas and effective cooling, it is preferred that the inert substance is filled into the whole inert substance layer substantially uniformly.

An inert substance of a single size, shape or material may be filled into the inert substance layer, or inert substances of two or more different sizes, shapes or materials may be filled into the inert substance layer. When two or more kinds of inert substances are used, a plurality of layers filled with inert substances different from each other may be stacked, or alternatively, the two or more kinds of inert substances may be mixed and filled into one layer. In the former case, it is preferred that the inert substances are filled so that each layer of the stacked layers is substantially uniform. In the latter case, it is preferred that the two or more kinds of inert substances are filled so that the whole layer is substantially uniform.

One of functions of the inert substance is to quench the acrolein-containing reaction gas to cool it to a temperature in the range suitable for an oxidation reaction in the second catalyst layer. Therefore, the inert substance layer has to have a length enough to sufficiently exert such a function. The length of the inert substance layer should be appropriately determined according to reaction conditions such as composition and concentration of the raw material gas and the reaction temperature, and cannot be determined to a specific value; however, it is preferably 100 mm or more, and more preferably 200 mm or more. In the case that a plurality of inert substance layers are stacked, the ratio between the layers can be appropriately set arbitrarily.

As to places to be filled with the inert substance, when using two reactors, the inert substance may be filled into the outlet side, relative to the gas flow direction. of the first reactor filled with the first catalyst and/or the inlet side, relative to the gas flow direction, of the second reactor filled with the second catalyst. Alternatively, the inert substance may be disposed in a pipe connecting the first reactor and the second reactor. When using one reactor, the inert substance may be disposed between the first catalyst layer and the second catalyst layer.

The first catalyst and the second catalyst used in the present invention are hereinafter explained. The first catalyst is not particularly limited as long as it can convert propylene to acrolein by gas-phase catalytic oxidation, and known oxide catalysts used in general can be used. Specifically, as the first catalyst, the oxide catalyst expressed by the following formula (I) can is preferably used:

$$Mo_aBi_bFe_cX1_dX2_eX3_fX4_gO_x \qquad (I)$$

wherein Mo is molybdenum; Bi is bismuth; Fe is iron; X1 represents at least one kind of element selected from the group consisting of cobalt and nickel; X2 represents at least one kind of element selected from the group consisting of alkali metals, alkali earth metals, boron and thallium; X3 represents at least one kind of element selected from the group consisting of tungsten, silicon, aluminum, zirconium and titanium; X4 represents at least one kind of element selected from the group consisting of phosphorus, tellurium, antimony, tin, cerium, lead, niobium, manganese, arsenic and zinc; O is oxygen; a, b, c, d, e, f, g and x mean atomic ratios of Mo, Bi, Fe, X1, X2, X3, X4 and O, respectively, and meet inequalities: a=12, 0.1≤b≤10, 0.1≤c≤20, 2≤d≤20, 0.001≤e≤10, 0≤f≤30 and 0≤g≤4, respectively; and x is a numeral value determined by oxidation states of respective elements.

The second catalyst is not particularly limited as long as it can convert acrolein to acrylic acid by gas-phase catalytic oxidation, and known oxide catalysts used in general can be used. Specifically, as the second catalyst, the oxide catalyst expressed by the following formula (II) can is preferably used:

$$Mo_hV_iW_jY1_kY2_lY3_mY4_nO_y \quad (II)$$

wherein Mo is molybdenum; V is vanadium; W is tungsten; Y1 represents at least one kind of element selected from the group consisting of antimony, bismuth, chromium, niobium, phosphorus, lead, zinc, cobalt, nickel and tin; Y2 represents at least one kind of element selected from the group consisting of copper and iron, Y3 represents at least one kind of element selected from the group consisting of alkali metals, alkali earth metals and thallium: Y4 represents at least one kind of element selected from the group consisting of silicon, aluminum, titanium, zirconium, yttrium, rhodium and cerium; O is oxygen; h, i, j, k, l, m, n and y mean atomic ratios of Mo, V, W, Y1, Y2, Y3, Y4 and O, respectively, and meet inequalities: h=12, 2≤i≤14, 0≤j≤12, 0≤k≤5, 0.01≤l≤6, 0≤m≤5 and 0≤n≤10, respectively; and y is a numeral value determined by oxidation states of respective elements.

As a forming method of these catalysts, conventionally well-known methods may be employed. For example, an extrusion molding method or a tablet compression method in each of which an active component is formed into a specific shape can be employed. Alternatively, the catalyst may be prepared by a supporting method for making any inert carrier having a specific shape support an active component.

A shape of the catalyst is not particularly limited, and any shape such as a spherical shape, a cylindrical shape, a ring shape, an irregular shape or the like, may be taken. Of course, the spherical shape does not have to be a true sphere and a substantially spherical shape will suffice. The same applies also to the cylindrical shape and the ring shape.

The first catalyst is filled into the first catalyst layer and the second catalyst is the second catalyst layer. As the first catalyst and the second catalyst, a single kind of catalyst may be used, respectively; alternatively, a plurality of kinds of catalysts different in a composition or shape may be used. For example, the first catalyst layer may be formed by stacking a plurality of layers filled with different first catalysts, or may be one layer filled with a mixture of two or more kinds of first catalysts. In addition, a part of the first catalyst may be diluted with an inert carrier or the like. The same applies also to the second catalyst.

As the fixed-bed reactor of the present invention, a fixed-bed multitubular heat-exchanging reactor can be used. As a reaction tube provided in the reactor, a general reaction tube with a circular cross-sectional shape may be used. An inner diameter of the reaction tube is not particularly limited as long as the catalyst and the inert substance can be filled therein; however, it is preferably 15 mm or more, more preferably 20 mm or more, even more preferably 22 mm or more, and preferably 50 mm or less, more preferably 40 mm or less, even more preferably 38 mm or less. A length of the reaction tube is determined depending on a capability of associated apparatuses and the like, and can be appropriately selected from a range of 1 m to 10 m.

Concerning a filling manner of the catalyst and the inert substance and reaction conditions, known methods disclosed in documents such as Japanese Unexamined Patent Application Publication Nos. 54-21966, 1-165543, 11-130722, except that the above-mentioned inert substance is used, can be employed.

Since the fixed-bed reactor of the present invention comprises the inert substance layer filled with the inert substance of the cylindrical shape having the surrounding wall in which the opening is formed, increase of the pressure loss in the inert substance layer of the fixed-bed reactor can be suppressed in producing acrylic acid by two-stage gas-phase catalytic oxidation of propylene. In addition, degradation of the second catalyst caused by introduction of molybdenum component sublimed from the first catalyst, by-produced high-boiling substances and the like into the second catalyst layer can be suppressed. Accordingly, stable production at a high yield is made possible for a long period as compared with conventional processes.

A process for producing acrylic acid of the present invention is hereinafter explained. The process for producing acrylic acid of the present invention is a process for producing acrylic acid comprising the step of producing acrylic acid from propylene by using the fixed bed reactor of the present invention. In detail, the process for producing acrylic acid of the present invention conducted by using the fixed bed reactor of the present invention, that comprises the steps of: producing acrolein by introducing propylene into the first catalyst layer to bring about gas-phase catalytic oxidation, as a first reaction step; introducing a reaction gas discharged from the first catalyst layer into the second catalyst layer through the inert substance layer; and producing acrylic acid by bringing about gas-phase catalytic oxidation of acrolein at the second catalyst layer. According to the process of producing acrylic acid of the present invention, since increase of the pressure loss in the inert substance layer is suppressed and degradation of the second catalyst due to by-produced high-boiling substances and the like, it is possible to stably produce acrylic acid for a long period. In addition, since degradation of the catalyst is suppressed, the yield of acrylic acid is enhanced.

Reaction temperatures suitable for the first reaction and the second reaction are appropriately adjusted according to the reaction conditions and the like. The reaction temperature of the first reaction is generally in the range of 300° C. or more and 380° C. or less, and the reaction temperature of the second reaction is generally 250° C. or more and 350° C. or less. Furthermore, the difference in the reaction temperatures between the first reaction and the second reaction is preferably in the range of 10° C. or more and 110° C. or less, and more preferably 30° C. or more and 80° C. less. The reaction temperatures of the first reaction and the second reaction substantially correspond to respective temperatures of heat medium at an inlet of the reactors or reaction zones, and the temperatures of heat medium at the inlet are determined according to the temperatures of the first reaction and the second reaction set within the above range.

EXAMPLES

The present invention will hereinafter be described more specifically by reference to Examples; however, the present invention is not limited to these Examples. The present invention can be put into practice after appropriate modifications or variations within a range meeting the gist of the present invention, all of which are included in the technical scope of the present invention. Hereinafter, the term "part(s) by mass" may be described simply as "part(s)" for convenience sake.

Conversion rate of propylene and an yield of acrylic acid were determined by the following equations:

Conversion rate of propylene (mol %)=(molar quantity of reacted propylene/molar quantity of fed propylene)×100

Yield of acrylic acid (mol %)=(molar quantity of produced acrylic acid/molar quantity of fed propylene)×100

(1) Experiment Example 1

(1-1) Preparation of a First Catalyst 1

2000 parts of distilled water was stirred while heating, and 500 parts of ammonium molybdate and 63.7 parts of ammonium paratungstate were dissolved therein (solution A). Separately, 295.4 parts of cobalt nitrate was dissolved in 500 parts of distilled water (solution B). Further separately, 30 parts of concentrated (65 mass %) nitric acid was added to 350 parts of distilled water to give an acidic solution, and 114.4 parts of ferric nitrate and 229 parts of bismuth nitrate were dissolved therein to give a solution C. The solutions B and C were added dropwise to the solution A, and then, to the obtained mixture, a solution obtained by dissolving 2.4 parts of potassium nitrate in 50 parts of distilled water was added, and 177 parts of silica sol (20 mass %) was further added to give a suspension liquid. The obtained suspension liquid was heated and stirred to vaporize the solvent. The resultant dry product was dried at 200° C. and then pulverized, and molded into a cylindrical shape having an outer diameter of 6 mm, an inner diameter of 2 mm, and a length of 6 mm. The obtained molded material was calcined at 460° C. for 8 hours under air flow to give a first catalyst 1. This first catalyst had the following metal element composition excluding oxygen:

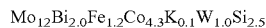

$Mo_{12}Bi_{2.0}Fe_{1.2}Co_{4.3}K_{0.1}W_{1.0}Si_{2.5}$ (1-2) Preparation of a Second Catalyst 1

2000 parts of distilled water was stirred while heating, and 350 parts of ammonium paramolybdate, 96.6 parts of ammonium metavanadate and 26.8 parts of ammonium paratungstate were dissolved therein. Separately, 200 parts of distilled water was stirred while heating, 63.9 parts of copper nitrate was dissolved therein. Thus obtained two solutions were mixed, and 28.9 parts of antimony trioxide was further added thereto to give a suspension liquid. The suspension liquid was evaporated to give a cake-like solid matter, and the solid matter was calcined at 380° C. for 5 hours. The calcined solid matter was pulverized to a particle diameter of 250 µm or less to give a powdery catalyst. Into a centrifugal fluidizing coating apparatus, 1150 parts of an α-alumina spherical carrier having an average particle diameter of 5 mm was fed and then the powdery catalyst was fed together with a 10 mass % ammonium nitrate aqueous solution as a binder with flowing hot air of 90° C. to make the carrier support the powdery catalyst. Then, the obtained supported catalyst was heated at 400° C. for 6 hours under an air atmosphere to give a second catalyst 1. The supported ratio of this catalyst was about 32 mass %, and the second catalyst 1 had the following metal element composition excluding oxygen:

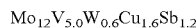

$Mo_{12}V_{5.0}W_{0.6}Cu_{1.6}Sb_{1.2}$

The supported ratio was determined by the following equations:

Supported ratio (mass %)=(mass of a catalyst (g)−mass of a used carrier (g))/mass of a used carrier (g)×100

(1-3) Reaction

A reactor having a reaction tube (whole length: 6000 mm, inner diameter: 25 mm) made of iron steel and a shell in which a heat medium is flowed and which covers the reaction tube was vertically-installed. A partition plate having a thickness of 30 mm that divides the shell into upper and lower spaces was installed at a position 3000 mm from the bottom of the shell, and the heat medium was flowed from bottom to top in the both upper and lower spaces. The first catalyst 1, an inert substance and the second catalyst 1 were filled in the reaction tube, by dropping the first catalyst 1, the inert substance and the second catalyst 1 in this order from the tops of the reaction tubes so that the layer lengths come to be 2800 mm for the first catalyst 1, 400 mm for the inert substance and 2800 mm for the second catalyst 1 in this order from the bottom of the reaction tube. The used inert substance was made of SUS410 and had a cylindrical shape of 7.5 mm outer diameter, 6.5 mm inner diameter and 7.5 mm length, having a surrounding wall in which one opening of 3.0 mm diameter was formed.

A mixed gas, as a raw material gas, consisting of 6.0 volume % of propylene, 12 volume % of oxygen, 25 volume % of steam and 57 volume % of nitrogen was introduced from the bottom of the reactor filled with the catalysts at a space velocity (STP) of 1600 relative to the first catalyst, thereby conducting gas-phase catalytic oxidation reaction. As to temperatures of the catalyst layers, a temperature of the first catalyst layer (a temperature of the heat medium at an inlet of the lower space) was 320° C., and a temperature of the second catalyst layer (a temperature of the heat medium at an inlet of the upper space) was 265° C. The results of the conversion rate of propylene and the yield of acrylic acid in the initial stage and after 4000 hours operation, and the increase amount of the pressure loss are shown in Table 1.

(2) Experiment Example 2

Gas-phase catalytic oxidation reaction was conducted in the same manner as in Experiment Example 1, except that the inert substance which was made of SUS 410 and had a cylindrical shape of 7.0 mm outer diameter, 6.5 mm inner diameter and 7.0 mm length, having a surrounding wall in which two openings of 4.0 mm diameter were formed, was used. The results of the reaction are shown in Table 1.

(3) Experiment Example 3

Gas-phase catalytic oxidation reaction was conducted in the same manner as in Experiment Example 1, except that the inert substance which was made of SUS 410 and had a cylindrical shape of 6.0 mm outer diameter, 5.5 mm inner diameter and 5.5 mm length, having a surrounding wall in which three openings of 4.0 mm diameter were formed, was used. The results of the reaction are shown in Table 1.

(4) Experiment Example 4

Gas-phase catalytic oxidation reaction was conducted in the same manner as in Experiment Example 1, except that the inert substance which was made of SUS 410 and had a cylindrical shape of 7.0 mm outer diameter, 6.5 mm inner diameter and 6.0 mm length, having a surrounding wall in which four openings of 4.8 mm diameter were formed, was used. The results of the reaction are shown in Table 1.

(5) Experiment Example 5

Gas-phase catalytic oxidation reaction was conducted in the same manner as in Experiment Example 1, except that the inert substance which was made of ceramic and had a cylindrical shape of 6.0 mm outer diameter, 5.0 mm inner diameter and 6.0 mm length, having a surrounding wall in which four openings of 3.0 mm diameter were formed, was used. The results of the reaction are shown in Table 1.

(6) Experiment Example 6

Gas-phase catalytic oxidation reaction was conducted in the same manner as in Experiment Example 1, except that the inert substance which was made of SUS 410 and had a cylindrical shape of 6.0 mm outer diameter, 5.0 mm inner diameter and 5.5 mm length, having a surrounding wall in which four openings of 4.5 mm diameter were formed, was used. The results of the reaction are shown in Table 1.

(7) Experiment Example 7

Gas-phase catalytic oxidation reaction was conducted in the same manner as in Experiment Example 1, except that the inert substance which was made of SUS 410 and had a cylindrical shape of 7.0 mm outer diameter, 6.5 mm inner diameter and 7.0 mm length, having a surrounding wall in which two openings of 1.8 mm diameter were formed, was used. The results of the reaction are shown in Table 1.

(8) Experiment Example 8

Gas-phase catalytic oxidation reaction was conducted in the same manner as in Experiment Example 2, except that the inert substance which was made of SUS 410 and had a cylindrical shape of 7.0 mm outer diameter, 6.5 mm inner diameter and 7.0 mm length, having a surrounding wall in which an opening was not formed, was used. The results of the reaction are shown in Table 1. In Experiment Example 8 in which the inert substance having a cylindrical shape without opening on the surrounding wall thereof was used, the yield of acrylic acid decreased and the increase amount of the pressure loss enlarged as compared with Experiment Examples 1 to 7 in which the same catalyst was used.

(9) Experiment Example 9

(9-1) Preparations of First Catalysts 2 and 3

2000 parts of distilled water was stirred while heating, and 500 parts of ammonium molybdate and 51 parts of ammonium paratungstate were dissolved therein (solution A). Separately, 240.4 parts of cobalt nitrate and 151 parts of nickel nitrate were dissolved in 500 parts of distilled water (solution B). Further separately, 30 parts of concentrated (65 mass %) nitric acid was added to 350 parts of distilled water to give an acidic solution, and 152.6 parts of ferric nitrate and 206 parts of bismuth nitrate were dissolved therein to give a solution C. These nitrate solutions of the solutions B and C were added dropwise to the solution A, and then, to the obtained mixture, a solution obtained by dissolving 1.9 parts of potassium nitrate in 50 parts of distilled water was added to give a suspension liquid. Thus obtained suspension liquid was heated and stirred to vaporize the solvent. The resultant dry product was dried at 200° C. and then pulverized, and molded into a cylindrical shape having an outer diameter of 6 mm, an inner diameter of 2 mm, and a length of 6 mm. The obtained molded material was calcined at 460° C. for 8 hours under air flow to give a first catalyst 2. As in the same manner described above, a first catalyst 3 having an outer diameter of 8 mm, an inner diameter of 3 mm, and a length of 7 mm was prepared. These first catalysts had the following metal element composition excluding oxygen:

$Mo_{12}Bi_{1.8}Fe_{1.6}Co_{3.5}Ni_{2.2}K_{0.08}W_{0.8}$ (9-2) Preparations of Second Catalysts 2 and 3

2000 parts of distilled water was stirred while heating, and 350 parts of ammonium paramolybdate, 106.3 parts of ammonium metavanadate and 44.6 parts of ammonium paratungstate were dissolved therein. Separately, 200 parts of distilled water was stirred while heating, 71.9 parts of copper nitrate was dissolved therein. Thus obtained two solutions were mixed, and 36.1 parts of antimony trioxide was further added thereto to give a suspension liquid. The suspension liquid was evaporated to give a cake-like solid matter, and the solid matter was calcined at 380° C. for 5 hours. The calcined solid matter was pulverized to a particle diameter of 250 μm or less to give a powdery catalyst. Into a centrifugal fluidizing coating apparatus, 1250 parts of an α-alumina spherical carrier having an average particle diameter of 5 mm was fed and then the powdery catalyst was fed together with a 10 mass % ammonium nitrate aqueous solution as a binder with flowing hot air of 90° C. to make the carrier support the powdery catalyst. Then, the obtained supported catalyst was heated at 400° C. for 6 hours under an air atmosphere to give a second catalyst 2. As in the same manner described above, a second catalyst 3 was prepared by using an α-alumina spherical carrier having an average particle diameter of 8 mm. The supported ratios of these catalysts were about 32 mass %, and these second catalysts had the following metal element composition excluding oxygen:

$Mo_{12}V_{5.5}W_{1.0}Cu_{1.8}Sb_{1.5}$ (9-3) Reaction

A reactor having a reaction tube (whole length: 6000 mm, inner diameter: 25 mm) made of iron steel and a shell in which a heat medium is flowed and which covers the reaction tube was vertically-installed. A partition plate having a thickness of 30 mm that divides the shell into upper and lower spaces was installed at a position 3000 mm from the bottom of the shell, and the heat medium was flowed from bottom to top in the both upper and lower spaces. The first catalyst 3, the first catalyst 2, an inert substance, the second catalyst 3 and the second catalyst 2 were filled in the reaction tube, by dropping the first catalyst 3, the first catalyst 2, an inert substance, the second catalyst 3 and the second catalyst 2 in this order from the tops of the reaction tubes so that the layer lengths come to be 800 mm for the first catalyst 3, 200 mm for the first catalyst 2, 400 mm for the inert substance, 700 mm for the second catalyst 3 and 2100 mm for the second catalyst 2 in this order from the bottom of the reaction tube. The used inert substance was made of SUS410 and had a cylindrical shape of 7.0 mm outer diameter, 6.5 mm inner diameter and 7.0 mm length, having a surrounding wall in which two openings of 4.0 mm diameter were formed.

A mixed gas, as a raw material gas, consisting of 8.0 volume % of propylene, 15 volume % of oxygen, 30 volume % of steam and 47 volume % of nitrogen was introduced from the bottom of the reactor filled with the catalysts at a space velocity (STP) of 2000 hr$^{-1}$ relative to the first catalyst, thereby conducting gas-phase catalytic oxidation reaction. As to temperatures of the catalyst layers, a temperature of the first catalyst layer (a temperature of the heat medium at an inlet of the lower space) was 325° C., and a temperature of the second catalyst layer (a temperature of the heat medium at an inlet of the upper space) was 268° C. The results of the conversion rate of propylene and the yield of acrylic acid in the initial stage and after 4000 hours operation, and the increase amount of the pressure loss are shown in Table 1.

(10) Experiment Example 10

Gas-phase catalytic oxidation reaction was conducted in the same manner as in Experiment Example 9, except that the inert substance which was made of SUS 410 and had a cylindrical shape of 7.0 mm outer diameter, 6.5 mm inner diameter and 7.0 mm length, having a surrounding wall in which an opening was not formed, was used. The results of the reaction are shown in Table 1. In Experiment Example 10 in which the inert substance having a cylindrical shape without opening on the surrounding wall thereof was used, the yield of acrylic acid decreased and the increase amount of the pressure loss enlarged as compared with Experiment Example 9 in which the same catalyst was used.

mm for the inert substance, 700 mm for the second catalyst 3 and 2100 mm for the second catalyst 2 in this order from the bottom of the reaction tube. The used inert substance was made of SUS410 and had a cylindrical shape of 7.0 mm outer diameter, 6.5 mm inner diameter and 7.0 mm length, having a surrounding wall in which two openings of 4.0 mm diameter were formed. A partition plate having a thickness of 50 mm that divides the shell into upper and lower spaces was installed at a position 3000 mm from the bottom of the shell, and the heat medium was flowed from bottom to top in the both upper and lower spaces.

A mixed gas, as a raw material gas, consisting of 9.0 volume % of propylene, 17 volume % of oxygen, 33 volume % of steam and 41 volume % of nitrogen was introduced from the bottom of the reactor filled with the catalysts at a space velocity (STP) of 1700 hr$^{-1}$ relative to the first catalyst, thereby conducting gas-phase catalytic oxidation reaction. As to temperatures of the catalyst layers, a temperature of the first catalyst layer (a temperature of the heat medium at an inlet of the lower space) was 325° C., and a temperature of the second catalyst layer (a temperature of the heat medium at an inlet of the upper space) was 270° C. The results of the conversion rate of propylene and the yield of acrylic acid in the initial stage and after 4000 hours operation, and the increase amount of the pressure loss are shown in Table 2.

TABLE 1

| | Size of Inert Substance | Opening | | | | Conversion Rate of | Yield of Acrylic | Increase of |
| | Outer Diameter (mm) × Inner Diameter (mm) × Length (mm) | Diameter (mm) | Number | Opening Ratio | Passage of Time | Propylene (mol %) | Acid (mol %) | Pressure Loss (kPa) |
|---|---|---|---|---|---|---|---|---|
| Experiment Example 1 | 7.5 × 6.5 × 7.0 (made of SUS410) | 3.0 | 1 | 0.04 | initial (48 Hr) 4000 Hr | 97.2 96.8 | 89.5 89.1 | — 3.8 |
| Experiment Example 2 | 7.5 × 6.5 × 7.0 (made of SUS410) | 4.0 | 2 | 0.16 | initial (48 Hr) 4000 Hr | 97.3 96.9 | 89.6 89.2 | — 3.2 |
| Experiment Example 3 | 6.0 × 5.5 × 5.5 (made of SUS410) | 4.0 | 3 | 0.36 | initial (48 Hr) 4000 Hr | 97.3 97.0 | 89.7 89.3 | — 3.1 |
| Experiment Example 4 | 7.0 × 6.5 × 6.0 (made of SUS410) | 4.8 | 4 | 0.55 | initial (48 Hr) 4000 Hr | 97.2 96.8 | 89.5 89.1 | — 3.5 |
| Experiment Example 5 | 6.0 × 5.0 × 6.0 (made of ceramic) | 3.0 | 4 | 0.25 | initial (48 Hr) 4000 Hr | 97.1 96.5 | 89.4 88.9 | — 3.6 |
| Experiment Example 6 | 6.0 × 5.0 × 5.5 (made of SUS410) | 4.5 | 4 | 0.61 | initial (48 Hr) 4000 Hr | 97.0 96.6 | 89.1 88.2 | — 4.3 |
| Experiment Example 7 | 7.0 × 6.5 × 7.0 (made of SUS410) | 1.8 | 2 | 0.03 | initial (48 Hr) 4000 Hr | 97.0 96.6 | 88.7 88.0 | — 4.5 |
| Experiment Example 8 | 7.0 × 6.5 × 7.0 (made of SUS410) | — | — | — | initial (48 Hr) 4000 Hr | 97.0 96.4 | 88.7 87.8 | — 4.8 |
| Experiment Example 9 | 7.0 × 6.5 × 7.0 (made of SUS410) | 4.0 | 2 | 0.16 | initial (48 Hr) 4000 Hr | 96.4 95.8 | 88.8 87.4 | — 5.6 |
| Experiment Example 10 | 7.0 × 6.5 × 7.0 (made of SUS410) | — | — | — | initial (48 Hr) 4000 Hr | 95.2 94.1 | 87.0 84.9 | — 8.4 |

(11) Experiment Example 11

Into a fixed-bed multitubular heat-exchanging reactor having 8,500 reaction tubes (reaction tube inner diameter: 25 mm, length 6000 mm) and a shell in which a heat medium is flowed and which covers the reaction tube, the first catalyst 3, the first catalyst 2, an inert substance, the second catalyst 3 and the second catalyst 2 were filled, by dropping the first catalyst 3, the first catalyst 2, an inert substance, the second catalyst 3 and the second catalyst 2 in this order from the tops of the reaction tubes so that the layer lengths come to be 800 mm for the first catalyst 3, 200 mm for the first catalyst 2, 400

TABLE 2

| | Passage of Time | Conversion Rate of Propylene (mol %) | Yield of Acrylic Acid (mol %) | Increase of Pressure Loss (kPa) |
|---|---|---|---|---|
| Experiment Example 11 | initial (48 Hr) 4000 Hr | 96.6 96.1 | 89.0 87.7 | — 5.2 |

REFERENCE SIGNS LIST 1. an outer diameter
2. an inner diameter
3. a length
4. an opening in a surrounding wall

The invention claimed is:

1. A fixed-bed reactor comprising:
   a first catalyst layer filled with a first catalyst for producing acrolein from propylene;
   a second catalyst layer filled with a second catalyst for producing acrylic acid from acrolein; and
   an inert substance layer provided between the first catalyst layer and the second catalyst layer, and filled with an inert substance of a cylindrical shape having a surrounding wall in which an opening is formed.

2. The fixed-bed reactor according to claim 1, wherein the surrounding wall of the cylindrical shape has an opening ratio of 0.04 or more and 0.60 or less, wherein the opening ratio is defined as follows:
   the opening ratio=an area of the opening / areas of an outer surface of the surrounding wall and the opening.

3. The fixed-bed reactor according to claim 1, wherein a cross-sectional shape of the cylindrical shape is substantially circle.

4. The fixed-bed reactor according to claim 3, wherein the cylindrical shape has an outer diameter of 3.0 mm or more and 10.0 mm or less, a length in an axial direction of 0.5 times or more and 2.0 times or less as much as the outer diameter, and an inner diameter of 0.5 times or more and 0.95 times or less as much as the outer diameter.

5. The fixed-bed reactor according to claim 1, wherein the inert substance is made of stainless-steel.

6. A process for producing acrylic acid, comprising the step of producing acrylic acid from propylene by using the fixed-bed reactor according to claim 1.

7. The fixed-bed reactor according to claim 1, wherein 2 to 6 holes are formed in the surrounding wall as the opening.

8. The fixed-bed reactor according to claim 1, wherein 1 to 4 holes are formed in the surrounding wall as the opening.

9. The fixed-bed reactor according to claim 1, wherein 1 to 6 holes are formed in the surrounding wall as the opening.

10. The fixed-bed reactor according to claim 1, wherein the opening(s) are not arranged so as to align in an axis direction of the cylindrical shape.

11. The fixed-bed reactor according to claim 1, wherein the openings are arranged in a circumferential direction of the cylindrical shape.

12. The fixed-bed reactor according to claim 1, wherein a length of the inert substance layer is 100 mm or more.

* * * * *